United States Patent
Rudek-Renaut et al.

(10) Patent No.: US 11,035,850 B2
(45) Date of Patent: Jun. 15, 2021

(54) QUANTITATIVE DETERMINATION OF NUCLEOSIDE ANALOGUE DRUGS IN GENOMIC DNA OR RNA

(71) Applicant: THE JOHNS HOPKINS UNIVERSITY, Baltimore, MD (US)

(72) Inventors: Michelle A. Rudek-Renaut, Fulton, MD (US); Srinivasan Yegnasubramanian, Ellicott City, MD (US); Nicole Anders, Pasadena, MD (US)

(73) Assignee: The Johns Hopkins University, Baltimore, MD (US)

( * ) Notice: Subject to any disclaimer, the term of this patent is extended or adjusted under 35 U.S.C. 154(b) by 124 days.

(21) Appl. No.: 16/092,233

(22) PCT Filed: Apr. 10, 2017

(86) PCT No.: PCT/US2017/026745
§ 371 (c)(1),
(2) Date: Oct. 9, 2018

(87) PCT Pub. No.: WO2017/180489
PCT Pub. Date: Oct. 19, 2017

(65) Prior Publication Data
US 2020/0041488 A1    Feb. 6, 2020

Related U.S. Application Data

(60) Provisional application No. 62/321,384, filed on Apr. 12, 2016.

(51) Int. Cl.
| | |
|---|---|
| *G01N 33/50* | (2006.01) |
| *A61K 31/706* | (2006.01) |
| *A61K 31/708* | (2006.01) |
| *A61K 31/7072* | (2006.01) |
| *C12Q 1/6872* | (2018.01) |
| *A61K 31/7076* | (2006.01) |
| *A61K 31/7064* | (2006.01) |
| *A61P 35/00* | (2006.01) |
| *G01N 30/72* | (2006.01) |

(52) U.S. Cl.
CPC ......... *G01N 33/502* (2013.01); *A61K 31/706* (2013.01); *A61K 31/708* (2013.01); *A61K 31/7064* (2013.01); *A61K 31/7072* (2013.01); *A61K 31/7076* (2013.01); *A61P 35/00* (2018.01); *C12Q 1/6872* (2013.01); *G01N 30/7233* (2013.01)

(58) Field of Classification Search
None
See application file for complete search history.

(56) References Cited

U.S. PATENT DOCUMENTS

| | | |
|---|---|---|
| 4,812,394 A | 3/1989 | Dolbeare et al. |
| 2008/0280774 A1 | 11/2008 | Burczynski et al. |
| 2009/0023149 A1 | 1/2009 | Knudsen |
| 2009/0285772 A1 | 11/2009 | Phiasivongsa et al. |

FOREIGN PATENT DOCUMENTS

| | | |
|---|---|---|
| EP | 1900823 A2 | 3/2008 |
| WO | 2009139888 | 11/2009 |

OTHER PUBLICATIONS

Xu et al., Development and validation of a liquid chromatography-tandem mass spectrometry method for quantification of decitabine in rat plasma Journal of Chromatography B vol. 899 pp. 81-85 (Year: 2012).*
Anders, N., et al., "Simultaneous quantitative determination of 5-aza-2'deoxycytidine genomic incorporation and DNA demethylation by liquid chromatography tandem mass spectrometry as exposure-response measures of iucleoside analog DNA methyltransferase inhibitors" Journal of Chromatography B, 1022 (2016) 38-45.
Oz, S., et al., "Quantitative determination of decitabine incorporation into DNA and its effect on mutation rates in iuman cancer cells" Nucleic Acids Research, 2014, vol. 42, No. 19 e152, doi: 10.1093/nar/gku775.
Agoston et al., "Increased protein stabililty causes DNA methyltransferase 1 dysregulation in breast cancer," J Biol Chem., May 6, 2005, 280(18):18302-18310.
Aimiuwu et al., "RNA-dependent inhibition of ribonucleotide reductase is a major pathway for 5-azacytidine activity in acute myeloid leukemia," Blood, May 31, 2012, 119(22):5229-5238.
Anders et al., "A robust and rapid liquid chromatography tandem mass spectrometric method for the quantitative analysis of 5-azacytidine," Biomed Chromatogr., Mar. 30, 2016, (3):494-496.
Azad et al., "The future of epigenetic therapy in solid tumours—lessons from the past," Nat Rev Clin Oncol., May 10, 2013, (5):256-266.
Baylin et al., "Alterations in DNA methylation: a fundamental aspect of neoplasia," Adv Cancer Res., 1998, 72:141-196.
Baylin et al., "Mechanisms underlying epigenetically mediated gene silencing in cancer," Semin Cancer Biol., Oct. 12, 2002, (5):331-337.
Chen et al., "A LC-MS/MS method for the analysis of intracellular nucleoside triphosphate levels," Pharm Res., Jun. 26, 2009, (6):1504-1515.
Christman et al., "5-Azacytidine and 5-aza-2'-deoxycytidine as inhibitors of DNA methylation: mechanistic studies and their implications for cancer therapy," Oncogene, Aug. 12, 21(35):5483-5495.
Derissen et al., "Concise drug review: azacitidine and decitabine," Oncologist, 2013, 18(5):619-624.
Derissen et al., "Quantitative determination of azacitidine triphosohate in peripheral blood mononuclear cells using liquid chromatography coupled with high-resolution mass spectrometry," J Pharm Biomed Anal., Mar. 2014, 90:7-14.
Estey et al., "Epigenetics in clinical practice: the examples of azacitidine and decitabine in myelodysplasia and acute myeloid leukemia," Leukemia, Sep. 27, 2013, (9):1803-1812.

(Continued)

*Primary Examiner* — Eric Olson
(74) *Attorney, Agent, or Firm* — Fish & Richardson P.C.

(57) ABSTRACT

This application provides methods to quantitate drug incorporation into DNA and of simultaneously measuring DNA methylation levels. Drugs include nucleoside analog DNA methyltransferase inhibitors.

24 Claims, 7 Drawing Sheets

(56) References Cited

OTHER PUBLICATIONS

Gardner et al., "Operating on chromatin, a colorful language where contect matters," J Mol Biol., May 27, 2011, 409(1):36-46.

Ghoshal et al., "5-Aza-deoxycytidin induces selective degradation of DNA methyltransferase 1 by a proteasomal pathway that requires the KEN box, bromo-adjacent homology domain, and nuclear localization signal," Mol Cell Biol., Jun. 2005, 25(11):4727-4741.

Gilbert et al., "The clinical application of targeting cancer through histone acetylation and hypomethylation," Clin Caner Res., Jul. 15, 2004, 10(14):4589-4596.

Haffner et al., "Androgen-induced TOP2B-mediated double-strand breaks and prostate cancer gene rearrangements," Nat Genet., Aug. 2010, 42(8):668-675.

Herman et al., "Gene silencing in cancer in association with promoter hypermethylation," N Engl J Med., Nov. 20, 2003, 349(21):2042-2054.

Hubeek et al., "The human equilibrative nucleoside transporter 1 mediates in vitro cytarabine sensitivity in childhood acute myeloid leukaemia," Br J Cancer, Dec. 12, 2005;93(12):1388-1394.

Issa et al., "Safety and tolerability of guadecitabine (SGI-110) in patients with myelodysplastic syndrome and acute myeloid leukaemia: a multicentre, randomised, dose-escalation phase 1 study," Lancet Oncol., Sep. 2015, 16(9):1099-1110.

Jansen et al., "Decitabine triphosphate levels in peripheral blood mononuclear cells from patients receiving prolonged low-dose decitabine administration: a pilot study," Cancer Chemother Pharmacol., Jun. 2012, 69(6):1457-1466.

Jones et al., "The epigenomics of cancer," Cell, Feb. 23, 2007, 128(4):683-692.

Jordheim et al., "Advances in the development of nucleoside and nucleotide analogues for cancer and viral diseases," Nat Rev Drug Discov., Jun. 2013, 12(6):447-464.

Kaminskas et al., "Approval summary: azacitidine for treatment of myelodysplastic syndrome subtypes," Clin Cancer Res., May 15, 2005, 11(10):3604-3608.

Kantarjian et al., "Decitabine improves patient outcomes in myelodysplastic syndromes: results of a phase III randomized study," Cancer, Apr. 15, 2006, 106(8):1794-1803.

Kissinger et al., "Determination of the antileukemia agents cytarabine and azacitidine and their respective degradation products by high-performance liquid chromatography," J Chromatogr., Feb. 26, 1986, 353:309-318.

Li et al., "Cytotoxicity and mode of action of 5-azacytidine on L1210 leukemia," Cancer Res., Nov. 1970, 30(11):2760-2769.

Liu et al., "Characterization of decomposition products and preclinical and low dose clincial pharmacokinetics of decitabine (5-aza-2'-deoxycytidine) by a new liquid chromatography/tandem mass spectrometry quantification method," Rapid Commun Mass Spectom., 2006, 20(7):1117-1126.

Liu et al., "Characterization of in vitro and in vivo hypomethylating effects of decitabine in acute myeloid leukemia by a rapid, specific and sensitive LC-MS/MS method," Nucleic Acids Res., 2007, 35(5):e31.

Lyko et al., "DNA methyltransferase inhibitors and the development of epigenetic cancer therapies," J Natl Cancer Inst., Oct. 19, 2005, 97(20):1498-1506.

Momparler et al., "Kinetics of phosphorylation of 5-aza-2'-deoxyycytidine by deoxycytidine kinase," Biochem Pharmacol., Apr. 15, 1979, 28(8):1443-1444.

Notari et al., "Kinetics and mechanisms of degradation of the antileukemic agent 5-azacytidine in aqueous solutions," J Pharm Sci., Jul. 1975, 64(7):1148-1157.

Oki et al., "Decitabine—bedside to bench. Crit Rev Oncol Hematol," Feb. 2007, 61(2):140-152.

PCT Internationa Search Report and Written Opinionin International Appln. No. PCT/US2017/026745, dated Jul. 20, 2017, 6 pages.

Rivard et al., "Phase I study on 5-aza-2'- deoxycytidine in children with acute leukemia," Leuk Res., 1981, 5(6):453-462.

Rogstad et al., "Chemical decomposition of 5-aza-2'-deoxycytidine (Decitabine): kinetic analyses and identification of products by NMR, HPLC, and mass spectrometry," Chem Res Toxicol., Jun. 2009, 22(6):1194-1204.

Rudek et al., "Pharmacokinetics of 5-azacitidine administered with phenylbutyrate in patients with refractory solid tumores or hematologic malignancies," J Clin Oncol., Jun. 10, 2005, 23(17):3906-3911.

Steensma et al., "Multicenter study of decitabine administered daily for 5 days every 4 weeks to adults with myelodysplastic syndromes: the alternative dosing for outpatient treatment (ADOPT) trial," J Clin Oncol., Aug. 10, 2009, 27(23):3842-3848.

Stresemann et al., "Modes of action of the DNA methyltransferase inhibitors azacytidine and decitabine," Int J Cancer., Jul. 1, 2008, 123(1):8-13.

Wang et al., "In vivo quantification of active decitabine-triphosphate metabolite: a novel pharmacoanalytical endpoint for optimization of hypomethylating therapy in acute myeloid leukemia," AAPS J, Jan. 2013, 15(1):242-249.

Zhao et al., "Quantification of 5-azacytidine in plasma by electrospray tandem mass spectrometry coupled with high-performance liquid chromatography," J Chromatogr B Analyt Technol Biomed Life Scie., Dec. 25, 2004, 813(1-2):81-88.

* cited by examiner

QUANTITATIVE DETERMINATION OF NUCLEOSIDE ANALOGUE DRUGS IN GENOMIC DNA OR RNA

CROSS-REFERENCE TO RELATED APPLICATIONS

This application is a 35 U.S.C. § 371 U.S. national entry of International Application PCT/US2017/026745 having an international filing date of Apr. 10, 2017, which claims the benefit of U.S. Provisional Application No. 62/321,384, filed Apr. 12, 2016, the content of each of the aforementioned applications is herein incorporated by reference in their entirety.

STATEMENT OF GOVERNMENTAL INTEREST

This invention was made with government support under grant no. P30CA006973, awarded by the National Institutes of Health. The government has certain rights in the invention.

BACKGROUND OF THE INVENTION

Epigenetic therapy is a promising approach in cancer therapy because aberrant DNA methylation plays a role in many cancer types. Decitabine (i.e., Dacogen, 5-aza-2'-deoxycytidine, DAC, aza-dC) is a classic epigenetic agent that is registered for the treatment for patients with myleodypastic syndrome (MDS). In addition, another DNA methyltransferase inhibitor 5-aza-2'-cytidine (i.e., Vidaza, 5AC, aza-C) has recently been approved by the Food and Drug Administration (FDA) as an antitumor agent for the treatment of myelodysplastic syndrome. DAC and 5AC undergo convergent metabolism by multiple nucleic acid metabolizing enzymes to produce intracellular aza-dCTP. In the case of 5AC, approximately 10-20% of the aza-CTP intermediate is converted to aza dCDP. DAC is a deoxycytidine analog that has a plasma half-life of only 15-25 minutes due to deamination to 5-aza-2'-deoxyuridine (aza-dU). After uptake in cells by nucleoside transporters, conversely, DAC is converted to its mono-, and subsequently di- and triphosphate (aza-dCMP, aza-dCDP, and aza-dCTP, respectively). The active metabolite aza-dCTP is incorporated into DNA leading to the inhibition of DNA methyltransferases (DNMT), thereby causing global DNA hypomethylation. Much effort has been spent on finding the optimal DAC or 5AC dose and dosing schedule to enhance the efficacy and minimize the toxicity of these drugs that inhibit DNMT.

SUMMARY OF THE INVENTION

This application provides a novel approach to quantitate drug incorporation into DNA and methods of simultaneously measuring DNA methylation levels.

A method of determining the amount of an agent incorporated in a nucleic acid (RNA or DNA) following exposure to a drug comprising the following steps: obtaining a biological material following exposure to a drug with a nucleic acid incorporating an agent; extracting the nucleic acid, preferably genomic nucleic acid, from the biological material; digesting the nucleic acid forming a first sample comprising dephosphorylated nucleotides; adding a stable heavy-isotope labeled internal standard to the first sample to form a second sample comprising an analyte; separating the analyte in the second sample using high pressure liquid chromatography through a porous graphite analytic column; adding the analyte to a mass spectrometer; and quantifying the amount of the analyte in the nucleic acid to determine the amount of agent in the nucleic acid. Preferred agents used in the present invention include 5-aza-2'-cytidine (5AC), 5-aza-2'-deoxycytidine (DAC) or a combination thereof. An example of a preferred drug used in the present invention is a nucleoside analog DNA methyltransferase inhibitor, preferably decitabine, azacitidine, guadecitabine or a combination thereof. The quantifying of the analyte step of the methods of the present invention is determined by using a standard curve and the amount of agent corresponds to the amount of the analyte being normalized to the amount of a natural DNA nucleoside in the nucleic acid. Suitable analytes that may be used in the present invention includes 5-aza-2'-deoxycytidine (DAC), 5-methyl-2'-deoxycytidine (5mC), 2'-deoxycytidine (2dC), or a combination thereof. The above method may also simultaneously quantify DNA methylation by quantifying the amount of 5-methyl-2'-deoxyctidine (5mC) with normalization to 2'-deoxycytidine (2dC) quantification. Suitable internal standard used in the present invention comprises 5-azacytidine-$^{15}N_4$ (5AC-$^{15}N_4$), 2'-deoxycytidine$^{13}C^{15}N_2$ (2dC-$^{13}C^{15}N_2$), and 5'-methyl-2'deoxycytidine-d3 (5mC-d3) in water. Suitable biological material used in the present invention includes blood, tissue, tumor, cell lines, or a combination thereof. Suitable digestion of nucleic acid occurs by sequentially exposing the nucleic acid to a nuclease and a phosphatase.

Another embodiment of the present invention includes a method of treating or preventing cancer in a subject comprising: administering to the subject an effective amount of a nucleoside analog DNA methyltransferase inhibitor that incorporates an agent into a nucleic acid of the subject, and salt, solvate, or stereoisomer thereof; obtaining a biological material of the subject with a nucleic acid incorporating an agent and natural DNA nucleosides; extracting the nucleic acid from the biological material; digesting the nucleic acid forming a first sample comprising dephosphorylated nucleotides; adding a stable heavy-isotope labeled internal standard to the first sample to form a second sample comprising an analyte; separating the analyte in the second sample using high pressure liquid chromatography through a porous graphite analytic column; adding the analyte to a mass spectrometer; and quantifying the amount of the analyte in the nucleic acid to determine the amount of agent in the nucleic acid.

"5AC" of "aza-C" is defined as 5-azacytidine.

"Azacitidine" (trade name Vidaza) is defined as 5-aza-2'-cytidine a drug used in the treatment of myelodysplastic syndrome.

"Decitabine" (trade name Dacogen) is defined as 5-aza-2'-deoxycytidine, a drug for the treatment of myelodysplastic syndromes and for acute myeloid leukemia (AML)

"2dC" is defined as 2'-deoxycytidine.

"DAC" or "aza-dC" is defined as 5-aza-2'-deoxycytidine.

"DNMT" is defined as DNA methyltransferase.

"Guadecitabine" is defined as decitabine deoxyguanosine or decitabine deoxyguanosine dinucleotide a cancer drug.

"MDS" is defined as myelodysplastic syndromes.

"5mC" is defined as 5'-methyl-2'deoxycytidine.

DETAILED DESCRIPTION OF THE INVENTION

Figure 1:
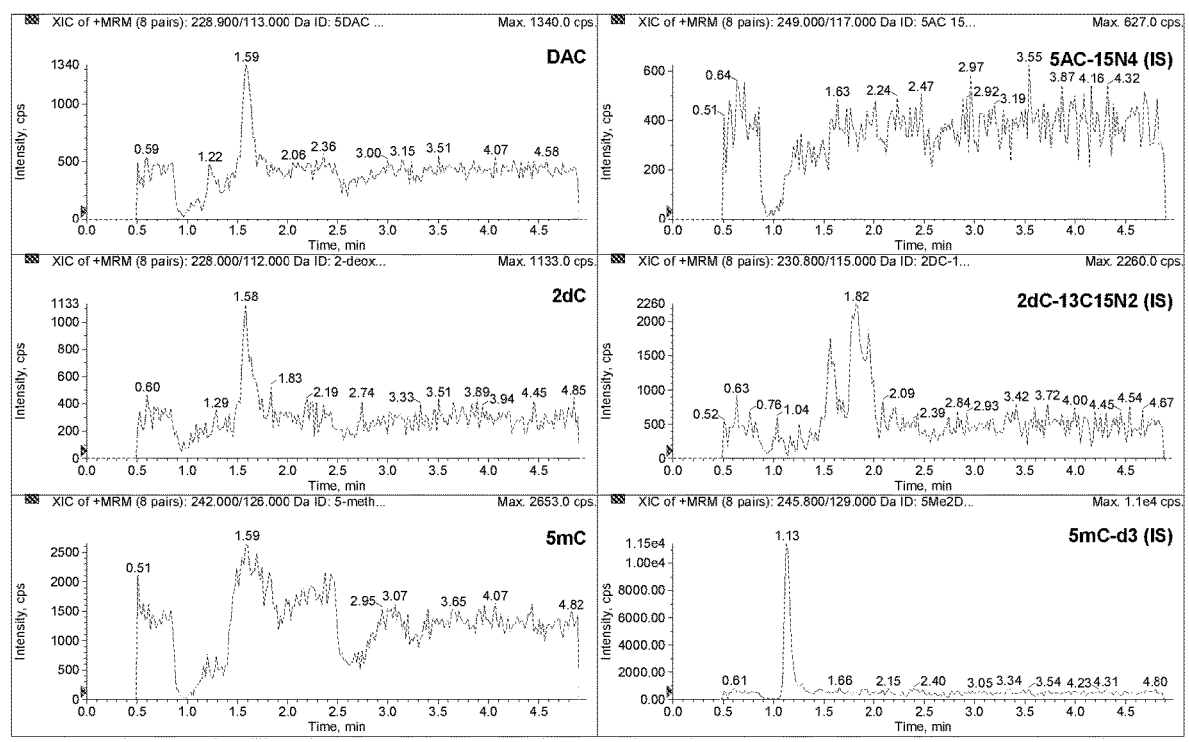
FIG. 1 illustrates representative chromatograms of blank matrix monitoring DAC, 2dC, 5mC, 5AC-$^{15}N_4$ (I.S.), 2dC-$^{13}C^{15}N_2$ (I.S.), and 5mC-d3 (I.S.).

Epigenetic silencing of genes that encode tumor suppressors, cell cycle regulators or proteins involved in cell-cell interaction occurs in both hematologic and epithelial malignancies. Such epigenetic silencing can occur by two distinct mechanisms: promoter methylation and histone modifications. The ability to induce gene re-expression by targeting these mechanisms is possible through pharmacological agents that impede promoter methylation by inhibiting DNA methyltransferases (DNMT) and agents that inhibit "readers", "writers" and "erasers" of histone modifications. Of these classes of epigenetic inhibitors, two nucleoside analog DNMT inhibitors are FDA approved for use in myelodysplastic syndromes (MDS), Vidaza (azacitidine) and Dacogen (decitabine). Given this initial success, these inhibitors were evaluated empirically in early phase clinical trials as single agents in numerous hematological and solid organ malignancies, but with very modest response rates. Despite the modest response rates, extensive research is being performed on the DNMT inhibitors with 207 active clinical trials being listed in clinicaltrials.gov. 5-azacytidine (5AC), 5-aza-2'-deoxycytidine (DAC), SGI-110 (DAC prodrug cleaved by phosphodiesterase) are nucleoside analogues that can either inhibit DNMT or be cytotoxic. Both proposed mechanisms of action require the incorporation into RNA (5AC) or DNA (DAC, DAC from 5AC or SGI-110) in lieu of cytidine. DAC, 5AC, SGI-110 must first undergo a large sequence of cellular and metabolic steps prior to becoming incorporated into genomic DNA. These steps include transport into the cell, conversion to DAC triphosphate through numerous enzymatic steps, and final incorporation as nucleotide monophosphates into the genomic DNA and RNA by polymerases. Once incorporated into DNA, these agents show dose responsive cytotoxicity, particularly at high doses, and inhibition of DNMT enzymes by covalently trapping the enzyme and inducing proteasomal degradation. However, because of the numerous steps involved, the degree to which a given dose in a given individual or cell system undergoes final incorporation into the genomic DNA and RNA can be variable, perhaps due to pharmacogenomics differences between individuals, presence of primary resistance mechanisms in cancer cells, or emergence of secondary resistance mechanisms during therapy. The level of incorporation in non-target tissues may also be useful for predicting therapeutic toxicity. The ability to measure the level of incorporation of the nucleoside analog DNMT inhibitors into genomic DNA or RNA would therefore have immense utility as an individualized measurement of exposure-response relationships. However, there were no prior technologies to facilitate measurement of the level of incorporation of the nucleoside analog DNMT inhibitors into genomic DNA (or RNA). We have developed a quantitative method for the incorporation of DAC into DNA normalized to the DNA base 2'-deoxycytidine (2dC). The method also facilitates quantitative measurement of global DNA methylation levels by quantifying 5-methyl-2'-deoxycytidine (5mC) with normalization to 2dC. The method exhibits exquisite selectivity, precision and accuracy. The method has been utilized in preclinical experiments to probe the mechanism of action of DAC and has demonstrated strong correlations between the incorporation and relevant pharmacodynamics effects such as demethylation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Methods

Materials:

All analytes purchased had a purity greater than 98%. 5mC, 5AC-$^{15}$N$_4$, 2dC-$^{13}$C$^{15}$N$_2$ and 5mC-d3 were purchased from Toronto Research Chemical (Canada). DAC and 2dC were purchased from Sigma Aldrich (USA).

Digest Procedures:

Genomic DNA was suspended in 50 µL of HPLC grade water, and digested with 4 Units of Nuclease P1 (Sigma Aldrich) at 65° C. for 10 minutes in a digestion buffer containing 0.04 mM DFAM, 3.25 mM ammonium acetate pH 5.0, 0.5 mM zinc chloride in a final volume of 100 µL. 20 µL of 100 mM Trizma base, pH 8.5 was added and this reaction was treated with 4 Units of Alkaline Phosphatase at 37° C. for 1 hour. Following incubation, 20 µL of 300 mM ammonium acetate, pH 5.0 and 6 µL of 0.25 mM DFAM/50 mM ethylenediaminetetraacetic acid was added to stop digestion.

LC/MS Method:

Standards and quality control (QCs) samples were prepared by adding known concentrations of analytes into blank digest matrix (all solvents used during the DNA digest except for the enzymes). All digested DNA samples, standards and QCs were prepared for analysis by adding 20 µL internal standard (5AC-$^{15}$N$_4$, 2dC-$^{13}$C$^{15}$N$_2$ and 5mC-d3 in water) to 100 µL of sample and vortex-mix briefly. The internal standard in the range of 5 µL, 10 µL, or 15 µL to 20 µL, 25 µL, 30 µL, or 35 µL could be added to a sample. The sample could be in the range of 85 µL, 90 µL, or 95 µL to 100 µL, 105 µL, 110 µL, or 110 µL. The samples were injected onto a LC-MS system containing a Waters Acquity UPLC (Milford, Mass.) interfaced with an AB Sciex 5500 triple quadruple mass spectrometer (Foster City, Calif.). Chromatographic separation was achieved using Thermo Hypercarb porous graphite analytical column (100×2.1 mm, 5 µm, Waltham, Mass.) running isocratic with 10 mM ammonium acetate-acetonitrile-formic acid (70:30:0.1, v/v) with a flow rate of 0.300 µL/mL. The mass spectrometer was run in positive electrospray ionization mode with follow MRM transitions: DAC: 228.9→113.0, 2dC: 228.0→112.0, 5mC: 242.0→126.0, 5AC-$^{15}$N$_4$ (internal standard): 249.0→117.0, 2dC-$^{13}$C$^{15}$N$_2$ (internal standard) 230.8→115.0 and 5mC-d3 (internal standard) 245.8→129.0. The calibration range was 2-400 ng/mL for DAC, 5-1,000 ng/mL for 5mC, and 50-10,000 ng/mL for 2dC. All analytes were quantified using quadratic regression with 1/x$^2$ weighing.

Cell Culture and Drug Treatment:

DU145 prostate cancer cells were cultured in RPMI-1640, supplemented with 5% fetal bovine serum (Invitrogen). DAC was dissolved in DMSO and added to the culture at varying concentrations. The same volume of DMSO was added as a control. Cells were allowed to grow for 48 hr. An independent experiment was performed in three replicates. Following cell harvest, genomic DNA isolation, digestion to single dephosphorylated nucleotides according to our described protocols, DAC and 2dC content were determined using our LC-MS/MS analytical approach.

Mice and Drug Treatment:

Nude mice were housed in a pathogen-free facility. All animal protocols were approved by the Johns Hopkins Animal Care and Use Committee. Male mice aged 8 to 10 weeks were used.

DAC (1, 2 or 5 mg/kg) (Sigma-Aldrich) or vehicle was administered via daily intraperitoneal injection. Doses were administered for two 1-week cycles consisting of every day administration for 5 days followed by two days of rest. Genomic DNA was collected from colon tissue and whole bone marrow cells, and subjected to digestion to single dephosphorylated nucleotides according to our protocols. DAC, 2dC, and 5mC were measured using our LC-MS/MS analytical approach.

Results:

Analytical Method

Figure 2:
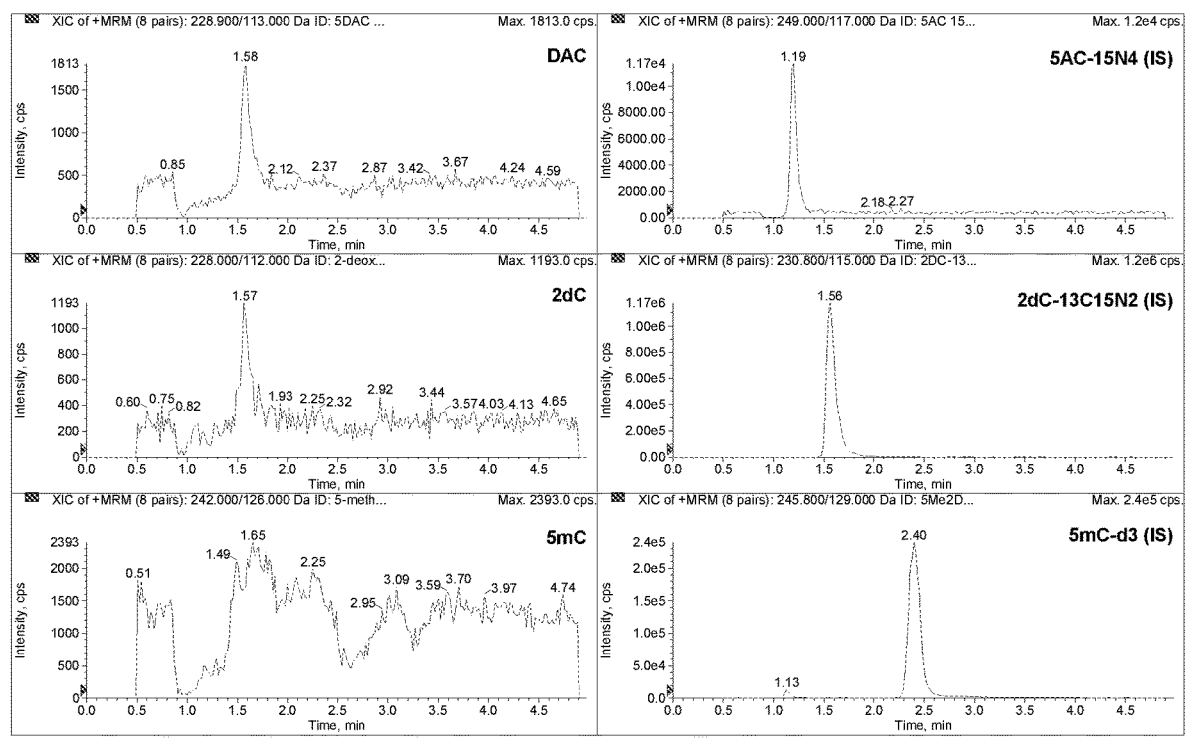
FIG. 2 illustrates representative chromatograms of blank matrix spiked with internal standard monitoring DAC, 2dC, 5mC, 5AC-$^{15}$N$_4$ (I.S.), 2dC-$^{13}$C$^{15}$N$_2$ (I.S.), and 5mC-d3 (I.S.).
Figure 3:
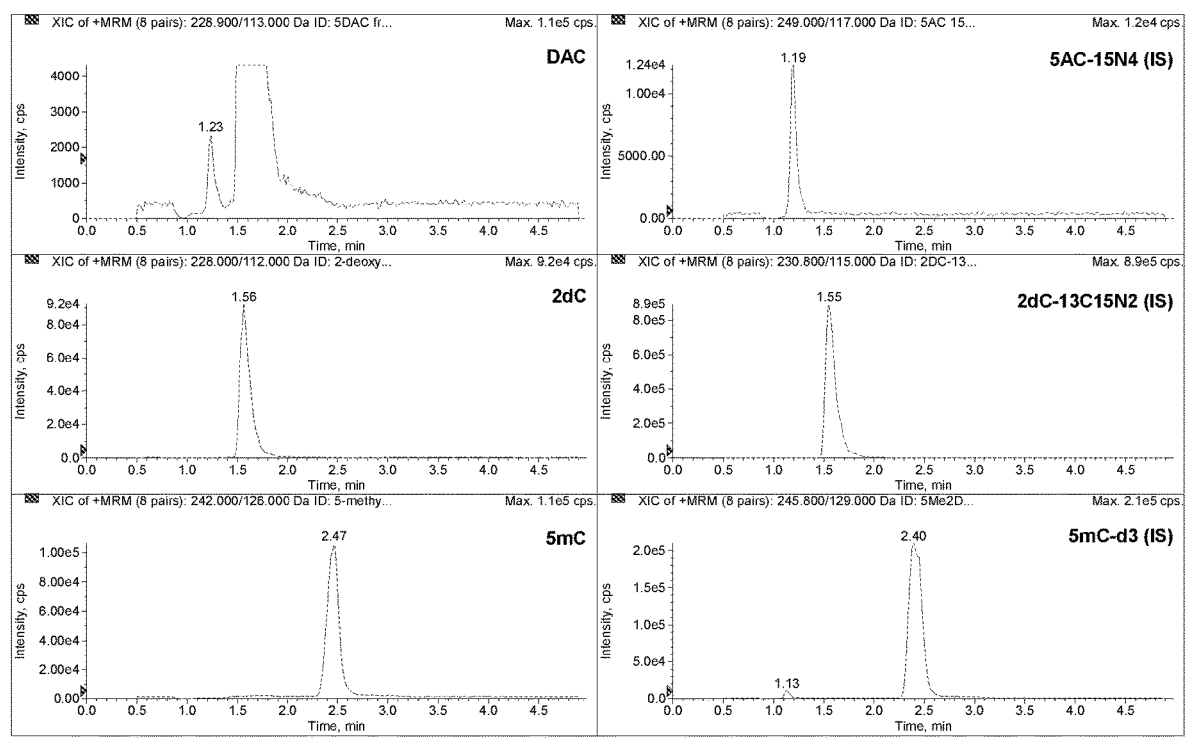
FIG. 3 illustrates representative chromatograms of the lowest calibration standard spiked with 2 ng/mL DAC, 5 ng/mL 5mC and 50 ng/mL 2dC monitoring DAC, 2dC, 5mC, 5AC-$^{15}$N$_4$ (I.S.), 2dC-$^{13}$C$^{15}$N$_2$ (I.S.), and 5mC-d3 (I.S.).
Figure 4:
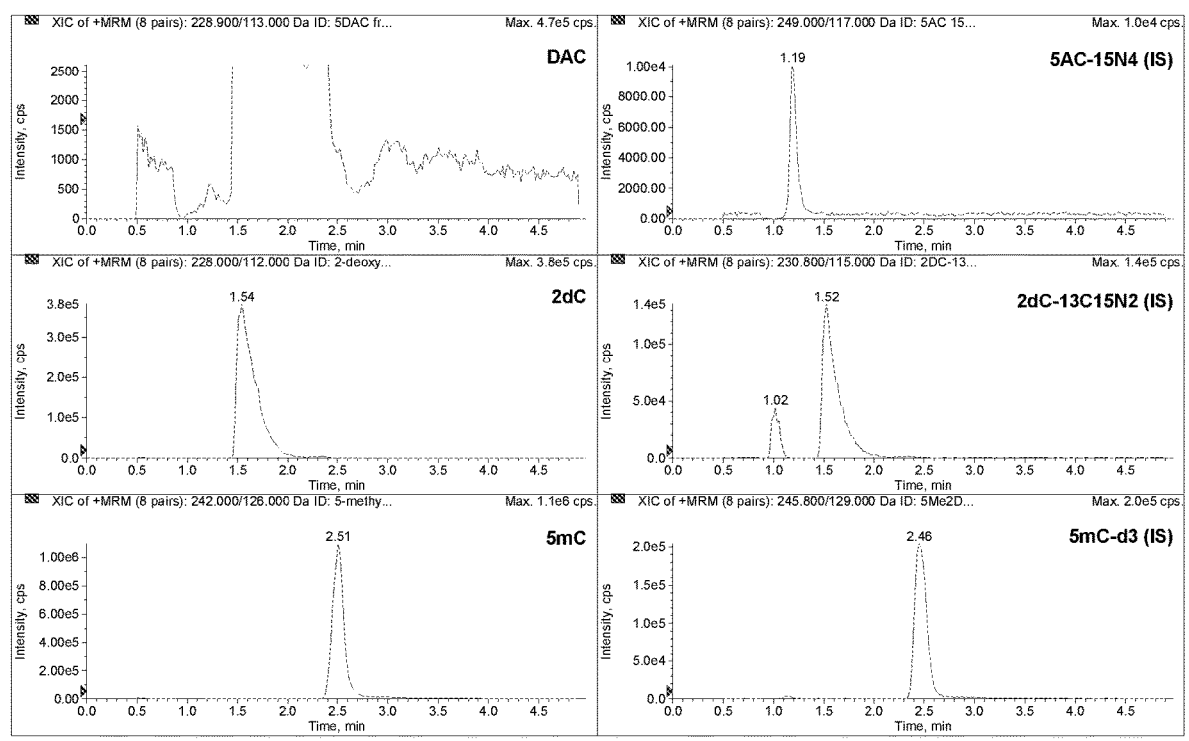
FIG. 4 illustrates representative chromatograms of DU145 cells that were untreated monitoring DAC, 2dC, 5mC, 5AC-$^{15}$N$_4$ (I.S.), 2dC-$^{13}$C$^{15}$N$_2$ (I.S.), and 5mC-d3 (I.S.). The concentrations of DAC, 5mC, and 2dC were below limits of quantitation (<2 ng/mL), 52.4 ng/mL, and 1790 ng/mL, respectively.
Figure 5:
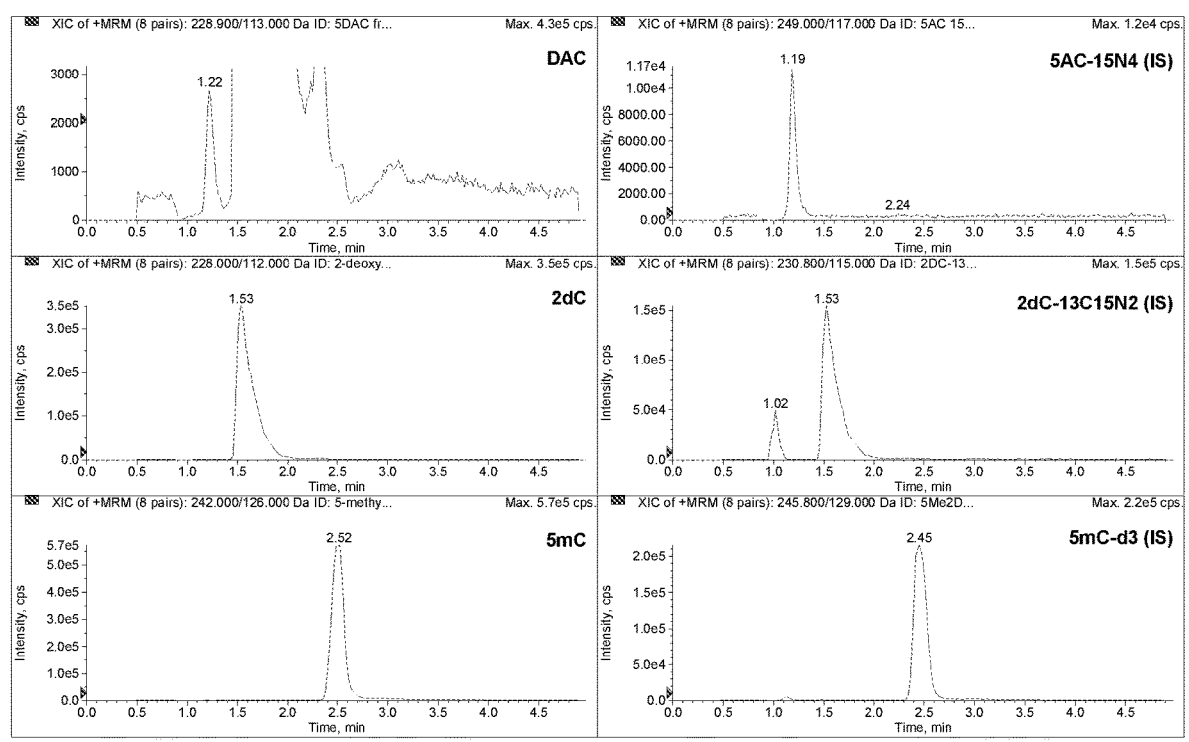
FIG. 5 illustrates representative chromatograms of DU145 cells treated with 500 nM DAC monitoring DAC, 2dC, 5mC, 5AC-$^{15}$N$_4$ (I.S.), 2dC-$^{13}$C$^{15}$N$_2$ (I.S.), and 5mC-d3 (I.S.). The concentrations of DAC, 5mC, and 2dC were 2.8 ng/mL, 27.4 ng/mL, and 1250 ng/mL, respectively.

A LC-MS/MS method was developed and validated to determine DAC, 2dC, and 5mC concentrations in DNA digest matrix (FIGS. 1-3). No major interferences were observed from blank matrix (FIGS. 1 and 2). The accuracy, within run and between run precision for all analytes are presented in Table 1. Preliminary stability experiments have been performed to ensure a robust analytical method and are presented in Table 2. Samples can be stored as the single dephosphorylated nucleotides for up to 35 days. The method has been applied in vitro to untreated (FIG. 4) and DAC treated cells (FIG. 5).

Figure 6:
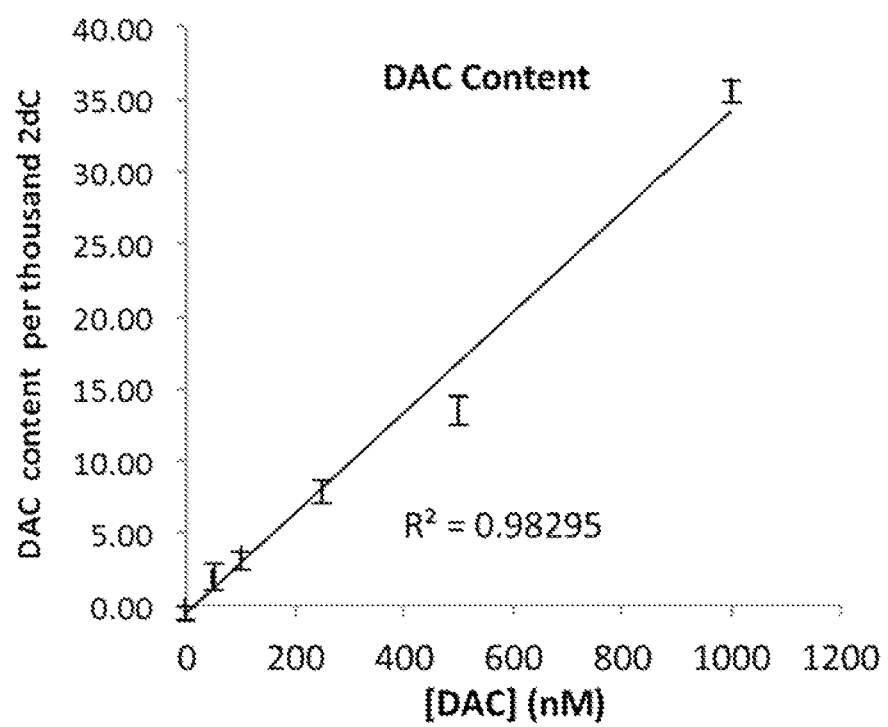
FIG. 6 illustrates incorporation of DAC into genomic DNA follows a linear correlation with dose of DAC exposure. DU145 human prostate cancer cells were treated with increasing doses of DAC for 48 hours. The amount of DAC per thousand 2dC showed a strong linear correlation with the initial treatment dose. Shown are the mean±standard error of the mean (SEM) of three replicate measurements.

Increasing DAC Exposure Results in an Increase in DNMT Inhibitor Incorporation into Genomic DNA When DU145 human prostate cancer cells were treated with increasing doses of DAC, the amount of DAC per thousand 2dC showed a strong linear correlation with the initial treatment dose (FIG. 6).

Figure 7:
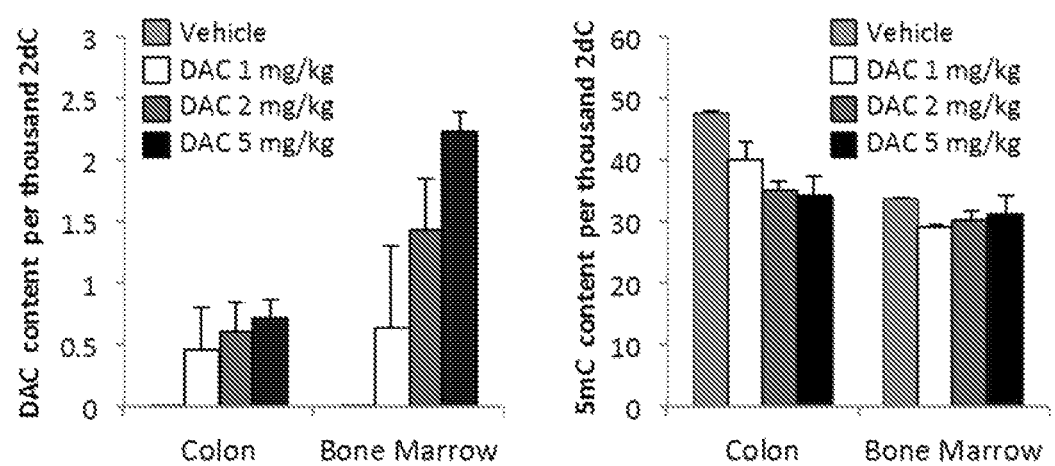
FIG. 7 illustrates DAC and 5mC content in genomic DNA of colon and bone marrow cells from mice treated with a dose response of DAC. Mice were treated with a dose response of DAC in normal saline at various doses for two 1-week cycles consisting of every day administration for 5 days followed by two days of rest. Results for DAC and 5mC content per thousand 2dC show a dose responsive increase in incorporation in colon and bone marrow cells with different efficiencies. Interestingly, while 5mC content was inversely correlated with DAC incorporation in colon cells, but not in bone marrow cells.

DNMT Inhibitor Incorporation into DNA is Observed in Mouse Colon and Bone Marrow Specimens After administration of 10 doses of DAC, there was a dose responsive increase in incorporation in colon and bone marrow cells with different efficiencies (FIG. 7). Interestingly, 5mC content was inversely correlated with DAC incorporation in colon cells but not in bone marrow cells. Taken together, our data suggests that 5mC measurement alone is a poor surrogate for understanding DAC incorporation due to complex cellular and tissue dynamics.

CONCLUSIONS AND FUTURE DIRECTIONS

To date, we have developed and analytical method to quantitate DAC, 2dC, and 5mC in genomic DNA. This method has been utilized in preclinical experiments to probe the mechanism of action of DAC. Preliminary results have shown strong correlations between increasing DAC dose exposure and incorporation into genomic DNA. Future experiments are planned to further interrogate the mechanism of action and inherent differences between all nucleoside analogue DNMT inhibitors. In addition, a method will be developed to assess 5AC incorporation into RNA to further probe that analogue's mechanism of action. 5AC also is metabolized by multiple nucleic acid metabolizing enzymes to produce aza-dCDP (a possible analyte) that is known to incorporate into DNA.

TABLE 1

Validation Characteristics for DAC, 2dC, and 5mC

| Analyte | Lower Limit of Quantitation | Low QC | Medium QC | High QC |
|---|---|---|---|---|
| DAC | 2 ng/mL | 3 ng/mL | 80 ng/mL | 320 ng/mL |
| Average ± St. Dev | 1.9 ± 0.0 | 2.9 ± 0.0 | 79.6 ± 1.1 | 315.4 ± 4.0 |
| Intra-Day Accuracy (%) | 90.6-95.6 | 94.3-96.5 | 98.0-100.8 | 97.2-99.6 |
| Intra-Day Precision (%) | 4.7-8.1 | 0.8-4.7 | 2.3-2.9 | 2.4-4.6 |
| Inter-Day Accuracy (%) | 93.0 | 95.4 | 99.4 | 98.6 |
| Inter-Day Precision (%) | 6.3 | 3.3 | 2.7 | 3.5 |
| 2dC | 50 ng/mL | 75 ng/mL | 2000 ng/mL | 8000 ng/mL |
| Average ± St. Dev | 49.2 ± 1.0 | 73.6 ± 1.1 | 2044.5 ± 88.7 | 7853.2 ± 482.4 |
| Intra-Day Accuracy (%) | 97.4-99.8 | 97.8-98.7 | 100.3-103.4 | 96.1-100.6 |
| Intra-Day Precision (%) | 1.2-2.6 | 1.3-1.9 | 3.8-4.9 | 3.7-8.3 |
| Inter-Day Accuracy (%) | 98.5 | 98.2 | 102.2 | 98.2 |
| Inter-Day Precision (%) | 2.0 | 1.6 | 4.3 | 6.1 |
| 5mC | 5 ng/mL | 7.5 ng/mL | 200 ng/mL | 800 ng/mL |
| Average ± St. Dev | 4.6 ± 0.1 | 7.4 ± 0.1 | 204.4 ± 1.2 | 801.7 ± 12.7 |
| Intra-Day Accuracy (%) | 96.2-99.8 | 96.2-99.9 | 101.8-102.9 | 98.8-101.9 |
| Intra-Day Precision (%) | 0.7-1.2 | 0.7-2.1 | 1.0-3.0 | 0.6-1.2 |
| Inter-Day Accuracy (%) | 98.1 | 98.0 | 102.2 | 100.2 |
| Inter-Day Precision (%) | 1.8 | 2.1 | 1.9 | 1.6 |

TABLE 2

Stability of DAC, 2dC, and 5mC*

| Analyte | Low QC | High QC | Stock Solution in Water |
|---|---|---|---|
| DAC | 3 ng/mL | 320 ng/mL | 1 mg/mL |
| Digest Buffers Stability (−70° C.) (35 Days) (%) | 101.8 | 103.2 | |
| Reinjection Stability (5 Days) (5° C.) (%) | 88.6 | 92.5 | |
| Stock Stability (−20° C.) (27 Days) (%) | | | 94.8 |
| 2dC | 25 ng/mL | 75 ng/mL | 1 mg/mL |
| Digest Buffers Stability (−70° C.) (35 Days) (%) | 107.2 | 99 | |
| Reinjection Stability (5 Days) (5° C.) (%) | 108.0 | 106.0 | |
| Stock Stability (27 Days) (%) | | | 98.7 |
| 5mC | 2.5 ng/mL | 7.5 ng/mL | 1 mg/mL |
| Digest Buffers Stability (−70° C.) (35 Days) (%) | 106.3 | 101.3 | |
| Reinjection Stability (5 Days) (5° C.) (%) | 100.8 | 100.4 | |
| Stock Stability (27 Days) (%) | | | 100.3 |

*Stability experiments are continuing for the digest buffer and stock solution.

The invention claimed is:

1. A method of determining the amount of an agent incorporated in a nucleic acid following exposure to a drug comprising the following steps:
    (a) obtaining a biological material following exposure to a drug with a nucleic acid incorporating an agent;
    (b) extracting the nucleic acid from the biological material;
    (c) digesting the nucleic acid forming a first sample comprising dephosphorylated nucleotides;
    (d) adding a stable heavy-isotope labeled internal standard to the first sample to form a second sample comprising an analyte;
    (e) separating the analyte in the second sample using high pressure liquid chromatography;
    (f) adding the analyte to a mass spectrometer; and
    (g) quantifying the amount of the analyte in the nucleic acid to determine the amount of agent in the nucleic acid.

2. The method of claim 1 wherein the agent is selected from the group consisting of 5-aza-cytidine (5AC), 5-aza-2'-deoxycytidine (DAC) or a combination thereof.

3. The method of claim 1 wherein the drug is a nucleoside analog DNA methyltransferase inhibitor.

4. The method of claim 3 wherein the nucleoside analog DNA methyltransferase inhibitor is selected from the group comprising decitabine, azacitidine, guadecitabine or a combination thereof.

5. The method of claim 1 wherein quantifying the amount of the analyte is performed using a standard curve.

6. The method of claim 5 wherein the amount of agent corresponds to the amount of the analyte being normalized to the amount of a natural DNA nucleoside in the nucleic acid.

7. The method of claim 1, wherein the analyte is selected from the group consisting of 5-aza-2'-deoxycytidine (DAC), 5-methyl-2'-deoxycytidine, 2'-deoxycytidine, or a combination thereof.

8. The method of claim 7, further comprising quantifying DNA methylation by quantifying 5-methyl-2'-deoxyctidine with normalization to 2'-deoxycytidine quantification.

9. The method of claim 1, wherein the internal standard comprises 5-azacytidine-15N4, 2'-deoxycytidine13C15N2 and 5'-methyl-2' deoxycytidine-d3 in water.

10. The method of claim 1 wherein the nucleic acid is DNA.

11. The method of claim 1 wherein the biological material is selected from the group consisting of blood, tissue, tumor, cell lines, or a combination thereof.

12. The method of claim 1 wherein digestion occurs by sequentially exposing the nucleic acid to a nuclease and a phosphatase.

13. A method of treating or preventing cancer in a subject comprising:
    (a) administering to the subject an effective amount of a nucleoside analog DNA methyltransferase inhibitor that incorporates an agent into a nucleic acid of the subject, and salt, solvate, or stereoisomer thereof;
    (b) obtaining a biological material of the subject with a nucleic acid incorporating an agent;
    (c) extracting the nucleic acid from the biological material;

(d) digesting the nucleic acid forming a first sample comprising dephosphorylated nucleotides;
(e) adding a stable heavy-isotope labeled internal standard to the first sample to form a second sample comprising an analyte;
(f) separating the analyte in the second sample using high pressure liquid chromatography;
(g) adding the analyte to a mass spectrometer; and
(h) quantifying the amount of the analyte in the nucleic acid to determine the amount of agent in the nucleic acid.

14. The method of claim 13 wherein the agent is selected from the group consisting of 5-aza-cytidine, 5-aza-2'-deoxycytidine, or a combination thereof.

15. The method of claim 13 wherein the nucleoside analog DNA methyltransferase inhibitor is selected from the group comprising decitabine, azacitidine, guadecitabine, any combination thereof.

16. The method of claim 13 wherein quantifying the amount of the analyte is performed using a standard curve.

17. The method of claim 13 wherein the amount of agent corresponds to the amount of the analyte being normalized to the amount of a natural DNA nucleoside in the nucleic acid.

18. The method of claim 13, wherein the analyte is selected from the group consisting of 5-aza-2'-deoxycytidine, 5-methyl-2'-deoxycytidine, 2'-deoxycytidine, or a combination thereof.

19. The method of claim 18, further comprising quantifying DNA methylation by quantifying 5-methyl-2'-deoxycytidine with normalization to 2'-deoxycytidine quantification.

20. The method of claim 13, wherein the internal standard comprises 5-azacytidine-15N4, 2'-deoxycytidine13C15N2 and 5'-methyl2'deoxycytidine-d3 in water.

21. The method of claim 13 wherein the nucleic acid is DNA.

22. The method of claim 13 wherein the biological material is selected from the group consisting of blood, tissue, tumor, cell lines, or a combination thereof.

23. The method of claim 13 wherein digestion occurs by sequentially exposing the nucleic acid to a nuclease and phosphatase.

24. The method of claim 13 wherein separating the analyte in the second sample using high pressure liquid chromatography occurs through a porous graphite analytic column.

* * * * *